(12) United States Patent
Mueller et al.

(10) Patent No.: US 10,716,613 B2
(45) Date of Patent: Jul. 21, 2020

(54) PHOTONIC PROBE APPARATUS WITH INTEGRATED TISSUE MARKING FACILITY

(71) Applicant: KONINKLIJKE PHILIPS N.V., Eindhoven (NL)

(72) Inventors: Manfred Mueller, Eindhoven (NL); Payal Keswarpu, Bangalore (IN); Vipin Gupta, Bangalore (IN); Celine Firtion, Surat (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1667 days.

(21) Appl. No.: 14/377,184

(22) PCT Filed: Feb. 8, 2013

(86) PCT No.: PCT/IB2013/051063
§ 371 (c)(1),
(2) Date: Aug. 7, 2014

(87) PCT Pub. No.: WO2013/121331
PCT Pub. Date: Aug. 22, 2013

(65) Prior Publication Data
US 2016/0066979 A1     Mar. 10, 2016

Related U.S. Application Data

(60) Provisional application No. 61/597,872, filed on Feb. 13, 2012.

(51) Int. Cl.
*A61B 18/14* (2006.01)
*A61B 5/00* (2006.01)
(Continued)

(52) U.S. Cl.
CPC ............. *A61B 18/14* (2013.01); *A61B 1/043* (2013.01); *A61B 5/0062* (2013.01);
(Continued)

(58) Field of Classification Search
None
See application file for complete search history.

(56) References Cited

U.S. PATENT DOCUMENTS

| 5,991,653 A | 11/1999 | Richards-Kortum et al. |
| 6,296,608 B1 | 10/2001 | Daniels et al. |

(Continued)

FOREIGN PATENT DOCUMENTS

| JP | 2004089533 A | 3/2004 | |
| JP | 2009-153828 | * 7/2009 | ............... A61B 1/06 |

(Continued)

OTHER PUBLICATIONS

Muro et al. , the sage manual on the funadamental use of surgical energy (FUSE), 2012.*

(Continued)

*Primary Examiner* — Carolyn A Pehlke
*Assistant Examiner* — Marjan Saboktakin

(57) ABSTRACT

The invention relates to a photonic probe apparatus and a method for probing tissue to detect and mark biological tissue with cancerous or precancerous states. The apparatus involves a probe for illuminating tissue and collecting light from an illuminated tissue region through the probe, a unit for analyzing collected light to determine whether a threshold measure of probability of a cancerous or precancerous lesion in the probed tissue region in contact with the probe is exceeded, and an integrated tissue marking facility which can be activated to mark the probed tissue region through the probe when the threshold measure is exceeded. The photonic probe apparatus and the method are especially suitable for probing regions in squamous and columnar epithelia to detect and mark regions with cervical cancer or cervical intraepithelial neoplasia (CIN).

10 Claims, 5 Drawing Sheets

(51) Int. Cl.
  *A61B 1/04* (2006.01)
  *A61B 90/00* (2016.01)
  *A61B 1/06* (2006.01)
  *A61B 1/07* (2006.01)
  *A61B 1/00* (2006.01)
  *A61B 17/00* (2006.01)
  *A61B 18/00* (2006.01)

(52) U.S. Cl.
  CPC .......... *A61B 5/0071* (2013.01); *A61B 5/0075* (2013.01); *A61B 5/0084* (2013.01); *A61B 5/7275* (2013.01); *A61B 5/7282* (2013.01); *A61B 5/742* (2013.01); *A61B 5/7405* (2013.01); *A61B 5/7475* (2013.01); *A61B 1/00165* (2013.01); *A61B 1/00179* (2013.01); *A61B 1/0623* (2013.01); *A61B 1/07* (2013.01); *A61B 2017/00473* (2013.01); *A61B 2018/00589* (2013.01); *A61B 2018/00982* (2013.01); *A61B 2090/3908* (2016.02); *A61B 2090/3937* (2016.02); *A61B 2560/0443* (2013.01); *A61B 2562/0238* (2013.01); *A61B 2576/00* (2013.01)

(56) References Cited

U.S. PATENT DOCUMENTS

| | | | |
|---|---|---|---|
| 6,722,371 | B1 | 4/2004 | Fogarty et al. |
| 2002/0166946 | A1 | 11/2002 | Iizuka et al. |
| 2003/0220640 | A1* | 11/2003 | Lee .................. A61B 10/0266 606/45 |
| 2007/0149851 | A1 | 6/2007 | Nakamura et al. |
| 2009/0103882 | A1 | 4/2009 | Melville et al. |
| 2009/0217932 | A1 | 9/2009 | Voegele |
| 2009/0234187 | A1 | 9/2009 | Higuchi et al. |
| 2009/0326384 | A1* | 12/2009 | Bigio .................. A61B 5/0075 600/476 |
| 2010/0168561 | A1* | 7/2010 | Anderson ............. A61B 17/32 600/424 |
| 2011/0160577 | A1 | 6/2011 | Kaji et al. |

FOREIGN PATENT DOCUMENTS

| | | | |
|---|---|---|---|
| JP | 2009153828 A | | 7/2009 |
| WO | WO199712553 | | 4/1997 |
| WO | WO 2006-076810 | * | 7/2006 |
| WO | WO2006076810 | | 7/2006 |
| WO | WO2009050667 | | 4/2009 |
| WO | WO2011084722 | | 7/2011 |

OTHER PUBLICATIONS

Chang et al, "Quantitative Physiology of the Precancerous Cervix in Vivo Through Optical Spectroscopy", Neoplasia, vol. 11, No. 4, p. 325-332, 2009.

Brockmeyer et al, "Persistent and Recurrent Cervical Dysplasia After Loop Electrosurgical Excision Procedure", American Journal of Obstetrics and Gynecology, vol. 192, 2005, p. 1379-1381.

Ramanujam et al, "Cervical Precancer Detection Using a Multivariate Statistsical Algorighm Based on Laser-Induced Fluorescence Spectra at Multiple Excitation Wavelengths", Photochemistry and Photobiology, vol. 64, No. 4, 1996, p. 720-735.

R. Nachabe, et al., "Estimation of Lipid and Water Concentrations in Scattering media with Diffuse Optical Spectroscopy from 900 to 1600 nm", Journal of Biomedical Optics 15(3), May/Jun. 2010, pp. 037015-1 through 037015-10.

R. Rouzier, et al., "Frozen Section Examination of the Endocervical Margin of Cervical Conization Speimens", Science Direct, Gynecological Oncology 90 (2003) pp. 305-309.

* cited by examiner

FIG. 1A  FIG. 1B  FIG. 1C
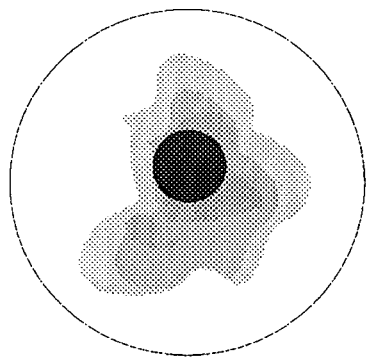
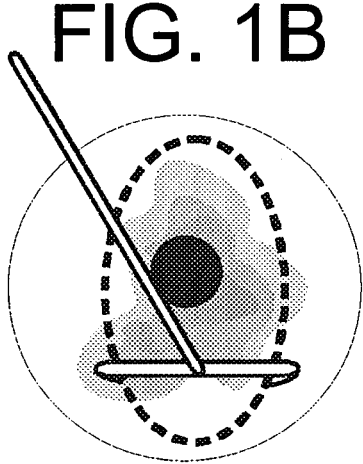
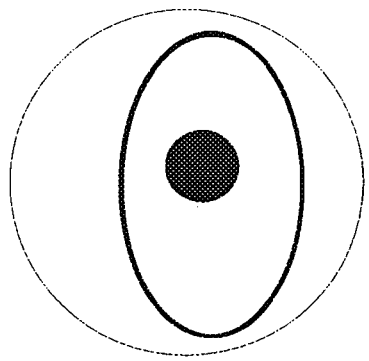
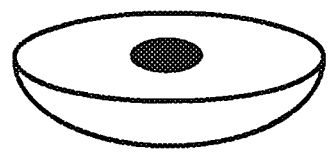

PHOTONIC PROBE APPARATUS WITH INTEGRATED TISSUE MARKING FACILITY

CROSS-REFERENCE TO PRIOR APPLICATIONS

This application is the U.S. National Phase application under 35 U.S.C. § 371 of International Application Serial No. PCT/IB2013/051063, filed on Feb. 8, 2013, which claims the benefit of U.S. application Ser. No. 61/597,872, Filed on Feb. 13, 2012. These applications are hereby incorporated by reference herein.

FIELD OF THE INVENTION

The invention relates to a photonic probe apparatus and a method for probing tissue to detect and mark tissue with cancerous or precancerous states. In particular, the invention relates to such photonic probe apparatus having an integrated tissue marking facility.

BACKGROUND OF THE INVENTION

Cancer that originates in squamous epithelia can develop in a large number of organs or tissues. The appearance of (pre)cancerous tissue can show very large differences depending on the body site, as can the difficulties and consequences related to excision of malignant tissue. This is especially relevant for cervical cancer which is the leading cause of cancer death in women in many developing countries and where the early detection and precise excision of malignant tissue are determining for the patient's ability to bear children afterwards.

A physician doing an excision procedure of a cervical cancer or cervical intraepithelial neoplasia (CIN) site faces two conflicting objectives: On one hand he wants to excise as little tissue as possible (especially if the patient wants to preserve her ability to bear children) on the other hand he has to excise all (pre-) cancerous tissue (with a safety margin) to avoid a recurrence. In practice however, the physician cannot directly see the lesion. Instead he/she has to rely on colposcopy images and/or on staining or marking techniques. The most commonly used marking technique for cervical cancer is acetowhitening. Both colposcopy images and acetowhitening are notoriously hard to interpret with large observer-to-observer variations. In addition, the acetowhite staining is transient, i.e. the white pattern will change while the excision takes place. FIGS. 1A-C schematically depicts an excision procedure of an ectocervical lesion; the black circle indicates the location of the cervical os. The exact extent of the lesion is unclear (1A), so the physician excises what he thinks is the approximate extent of the lesion (1B). After the excision (1C) the acetowhite is no longer visible on the remaining or the excised tissue, so there is no direct feedback to the physician on whether he/she was successful. The patient has to wait for the histopathology report.

Also these methods provide only information about tissue which can be assessed visually. For e.g. cervical cancer this will be the Ectocervix (which is all that is visible with the aid of a colposcope). How far a lesion extends into the endocervix is not known. Even a very experienced physician will be confident only of the approximate lateral extension of the lesion he/she is trying to remove. How deep it has to be removed remains a guess work. Most physicians will have to try to do a precise excision while actually being virtually blind.

In acetowhitening, 3-5% acetic acid produces a coagulation reaction with cells which is proportional to the content of nuclear protein in the cell. This reaction produces a noticeable effect compared with the normal pinkish color of the surrounding epithelium that is commonly visible to the naked eye.

With low-grade CIN, the acetic acid must penetrate into the lower one-third of the epithelium (where most of the abnormal cells with high nuclear density are located). Hence, the appearance of the whiteness is delayed and less intense due to the smaller amount of nuclear protein compared to areas with high-grade CIN or preclinical invasive cancer. Areas of high-grade CIN and invasive cancer turn densely white and opaque immediately after application of acetic acid, due to their higher concentration of abnormal nuclear protein and the presence of large numbers of dysplastic cells in the superficial layers of the epithelium.

The acetowhite appearance is not unique to CIN and early cancer. It is also seen in other situations when increased nuclear protein is present: for example in immature squamous metaplasia, congenital transformation zone, in healing and regenerating epithelium (associated with inflammation), leukoplakia (hyperkeratosis) and condyloma. While the acetowhite epithelium associated with CIN and preclinical early invasive cancer is more dense, thick and opaque with well demarcated margins from the surrounding normal epithelium, the acetowhitening associated with immature squamous metaplasia and regenerating epithelium is less pale, thin, often translucent, and patchily distributed without well-defined margins. Acetowhitening due to inflammation and healing is usually distributed widely in the cervix, not restricted to the transformation zone. The acetowhite changes associated with immature metaplasia and inflammatory changes quickly disappear, usually within 30-60 seconds.

Acetowhitening associated with CIN and invasive cancer quickly appears and persists for more than one minute. The acetic acid effect reverses much more slowly in high-grade CIN lesions and in early pre-clinical invasive cancer than in low-grade lesions, immature metaplasia and sub-clinical HPV changes. It may last for 2-4 minutes in the case of high-grade lesions and invasive cancer.

In short, acetowhitening correlates with the content of nuclear protein in the cells, and thus marks all tissue states having a substantially increased level of nuclear protein. The appearance of the acetowhite (density, intensity, opaqueness) depends on the type and exact location of the nuclear protein as well as on the time after application of the acetic acid (delay and decay of whitening). For suspected cervical cancer, acetowhitened tissue regions are notoriously hard to interpret and only the Ectocervix is marked up. How far a lesion extends into the endocervix cannot be determined.

In conclusion, in present methods applying acetowhitening during excising procedures, acetowhitening simultaneously detects and marks potential (pre)cancerous tissue. The application of acetic acid first marks up tissue with elevated nuclear protein content, all of which is potentially (pre)cancerous tissue, where after the physician evaluates which of the marked up tissue is actually (pre)cancerous based on his her level of skill and experience. Acetowhitening thereby involves the main disadvantages that it is very difficult to apply any objective threshold in the classification of the malignancy of the tissue and that the marking is not permanent leading to practical difficulties when performing excision procedures. Additionally, the endocervix is difficult to mark up, and especially it will be difficult to detect marked tissue in the endocervix.

The inventor of the present invention has appreciated that an improved methodology and apparatus for detecting and marking cancerous tissue is of benefit, and has in consequence devised the present invention.

SUMMARY OF THE INVENTION

It would be advantageous to achieve a methodology and an apparatus for detecting and marking cancerous tissue which can improve the classification of the tissue. It would also be advantageous to achieve a methodology and an apparatus for detecting and marking cancerous tissue which can simplify the excising procedure. In general, the invention preferably seeks to mitigate, alleviate or eliminate one or more of the above mentioned disadvantages singly or in any combination.

To better address one or more of these concerns, a first aspect of the invention provides a photonic probe apparatus for marking biological tissue in vivo, in particular squamous and columnar epithelia, in accordance with claim 1.

In contrast to the prior art techniques applying acetowhitening where the coagulation reaction initiated by the acetic acid both detects and marks potentially (pre)cancerous tissue, the photonic probe of the present invention allows for the detecting and the marking of (pre)cancerous tissue to be decoupled, or in other words, performed in separate and independent steps. The present invention allows for that (pre)cancerous tissue is first detected using a photonic probe and electronic data analysis and then marked using a marking facility integrated in the photonic probe that is activated upon detection of (pre)cancerous tissue. This involves at least the following effects and advantages:

The use of the photonic detection and electronic data analysis provides the effect that quantitative data related to the physiological composition of probed tissue can be gathered and analyzed by a computer. This is advantageous since it allows applying objective numerical parameters and thresholds in the tissue characterization and classification, thus removing the problems of inter- and intra-observer variations.

The decoupling of the detecting and marking of (pre) cancerous tissue provides the effect that a detailed classification of the tissue can be performed before a decision of marking is taken. Thus potential (pre)cancerous tissue that turns out not to be (pre)cancerous tissue will not be marked. This is advantageous since it allows for only marking tissue which should also be excised, thus simplifying the excising procedures.

The decoupling further provides freedom in selecting marking technique which is advantageous since it allows selecting marking techniques which e.g. are more permanent and/or which do not interfere with the continued detection of (pre)cancerous tissue.

The photonic probe applies electromagnetic radiation (EMR) of one or more wavelengths from the infrared to ultraviolet spectral ranges. Infrared EMR outside the visible is commonly also referred to as infrared light, and ultraviolet EMR outside the visible is commonly also referred to as ultraviolet light. Thus, in the present context, the term light is intended comprise ultraviolet light, visible light, and infrared light.

The photonic probe apparatus may apply one or more of the following techniques: diffuse optical spectroscopy, near-infra red spectroscopy, absorption spectroscopy, fluorescence spectroscopy, Raman spectroscopy, absorption spectroscopy, time-resolved spectroscopy. Each of these techniques, or a combination of two or more of these techniques, may be used to provide clinically relevant information about the physiological composition of tissues. They may, for instance, correlate with the intra/extra cellular content of one or more substances in order to give a precise fingerprint of the physiological composition of the tissue and/or allow a computer aided tissue classification with less observer-to-observer variation. For this purpose, the light source and the light sensor are configured to detect an intensity of collected light at different wavelengths to record a spectrum and wherein the threshold measure is related to the size of one or more peaks in the recorded spectrum. The different wavelengths for the spectra can be realized in different ways. For e.g. fluorescence spectroscopy, one can keep the wavelength of the excitation light constant and detect the emitted light at a plurality of wavelengths, one can keep the wavelength at which one detects the emitted light constant while using a plurality of excitation wavelengths, or one can use a use a plurality of both emission and excitation wavelengths. Similarly to obtain a spectra of the diffuse reflectance one can illuminate the tissue simultaneously with a plurality of wavelengths (white light) and spectrally resolve the collected light using e.g. a prism or a grating, or one can illuminate the tissue sequentially with different wavelengths of monochromatic light (e.g. by sweeping a laser or rotating a dispersive element such as a grating). Another way would be to simultaneously illuminate the tissue with light of different wavelengths whereby the different light wavelengths are modulated differently so that the detector can pick apart the contributions from the different wavelengths to the total detected light intensity.

In a preferred embodiment, determining a measure of probability of cancerous or precancerous lesions may involve distinguishing precancerous and/or cancerous tissue from not precancerous tissue based on the output signal from the light sensor. Such distinguishing is typically not definite. Rather, it is determined with a certain sensitivity and specificity which are examples of measures of probability of cancerous or precancerous lesions. In this embodiment, not precancerous tissue involves both healthy and abnormal tissue, such as inflammations, etc. A number of applicable embodiments for performing such distinction will be described later.

By connecting the electronic processor to control the tissue marking facility, the computer program may be configured to automatically activate the tissue marking facility to mark tissue when the threshold measure is exceeded. It will be appreciated that this is advantageous as the computer program can react very fast to the detection of (pre)cancerous tissue, so that such tissue is marked immediately, before the probe is moved away from the tissue. This facilitates a relatively fast scanning of the probe of the tissue to be investigated. Additionally, or alternatively, the photonic probe apparatus further comprises an audio and/or visual output connected to the electronic processor, which is activated to indicate to a user whether the threshold measure is exceeded and/or the state or a classification of the tissue currently being probed. Thereby, the user, or persons monitoring the process, can easily see the state of the currently probed tissue region, which can help to give an overview, especially when probing tissue regions that are difficult to see, such as subcutaneous tissue layers or in crevasses or cavities, e.g. in the endocervix or in the cervic os. This would also allow for the user to deactivate the automatic marking as controlled by the computer program, and manually mark detected (pre)cancerous tissue instead. For this and other purposes, the probe may further comprise an interface, typically a button on the probe, allowing a user to activate the integrated tissue marking facility to mark tissue. Such interface could also be used during automatic marking, in case the user finds non-(pre)cancerous tissue regions that should be excised for other reasons.

Marking the tissue is not trivial. The marking has to be clearly visible, it has to be localized (i.e. it may not run to other parts of the tissue), and it should not interfere with the optical measurement. In a preferred embodiment, the tissue marking facility comprises a cartridge for holding a marking substance and means for administering the marking substance through an output in the probe to dye tissue in contact with the probe. A marking substance is preferably a liquid or solid dye, such as inks and powdered solid dyes, or can be chemical marking substances engaging in chemical reactions with the compounds/substances in the tissue. If one uses ink, there may remain some ink stains on the probe which should not be allowed to distort the optical measurement. Also, one would want to be able to re-measure marked areas, i.e. if one measures again an area which has already been marked the device should again recognize the area as (pre)cancerous lesion (although one might want to keep the probe from further marking already marked areas).

In one preferred embodiment the marking substance comprises blue ink, such as Methylene blue. This provides the effects of a permanent, blue marking with clearly visible contrast on squamous and columnar tissue and which has the advantages of being cheap and non-toxic. Similar effects and advantages may potentially be obtained by using other blue inks with similar properties. Also, blue ink absorbs mostly between 630 nm and 800 nm, where there are no important absorption peaks for tissue chromophores (or fluorophores). Therefore blue ink is unlikely to interfere with measurement (actually one can probably ignore the absorption range of the blue ink used completely).

In another preferred embodiment, the marking substance comprises a luminescent dye, for example eosin. Luminescent dyes provide the advantage that they can be visible also when administered only to subcutaneous tissue layers or in crevasses or cavities such as in the endocervix or in the cervic os.

In an alternative implementation, the tissue marking facility applies a physical marking of the tissue, such as coagulation, or burning/carbonization. Here, the tissue marking facility may comprise an electric current source connected to supply an output electrode situated in the probe with sufficient current to coagulate tissue in contact with the probe. setups comprising applicable current sources and electrodes may be found within the field of electro-surgery devices.

It may be preferred that a probe tip is replaceable, so that it can be replaced after each use. In this case, it is preferred that the light source, light sensor and tissue marking facility works through the tip of the probe. Alternatively, this may be formulated as that the illumination of, collecting light from, and marking of tissue works through the tip of the probe. Such replaceable tip provides the advantage that it obviates or simplifies sterilization issues.

Therefore, in a second aspect, the invention provides a replaceable tip in accordance with claim 13 for a probe of a photonic probe apparatus, such as an apparatus in accordance with the first aspect. In a preferred embodiment, the replaceable tip further comprises a cartridge for holding a marking substance and means for administering the marking substance through the output for the tissue marking facility. Alternatively, the output for the tissue marking facility comprises an electrode connected to an electric current source of the tissue marking facility, where the output electrode is arranged to be in contact with tissue contacted by the replaceable tip when attached to the probe.

In another aspect, the invention relates to a method for marking a tissue region in a patient for excision, the method comprising:

providing a probe for illuminating tissue and collecting light from an illuminated tissue region through the probe and a tissue marking facility having an output integrated in the probe;

contacting tissue in the patient with the probe sensing and analyzing light collected from a tissue region through the probe to determine whether a threshold measure of probability of a cancerous or precancerous lesion in the tissue region is exceeded; and activating the tissue marking facility to mark the tissue region through the probe if the threshold measure is exceeded.

This method will primarily be embodied via the following description of the photonic probe and its use.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1A-C schematically depicts a prior art excision procedure of an ectocervical lesion.

DESCRIPTION OF EMBODIMENTS

Figure 2C:
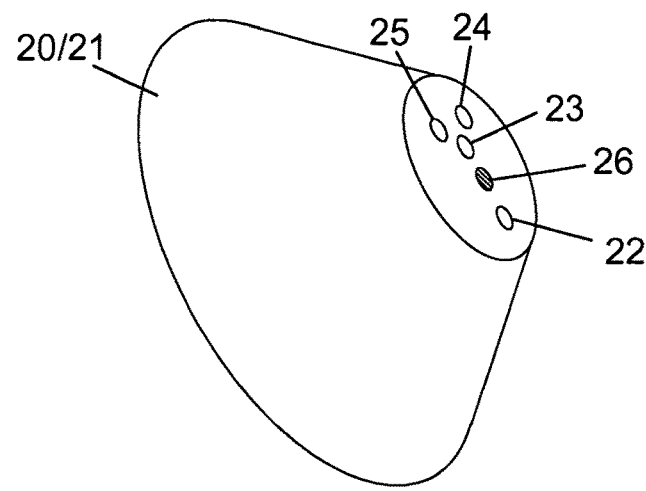
FIG. 2A-C illustrates a photonic probe apparatus according to an embodiment of the invention.
Figure 2B:
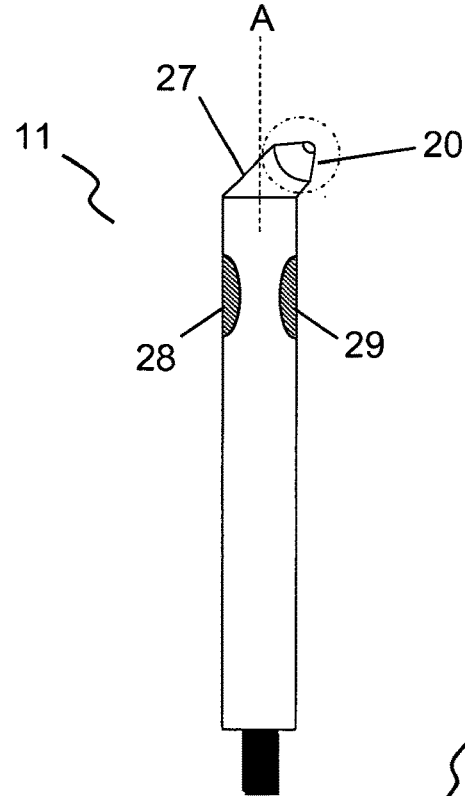
Figure 2A:
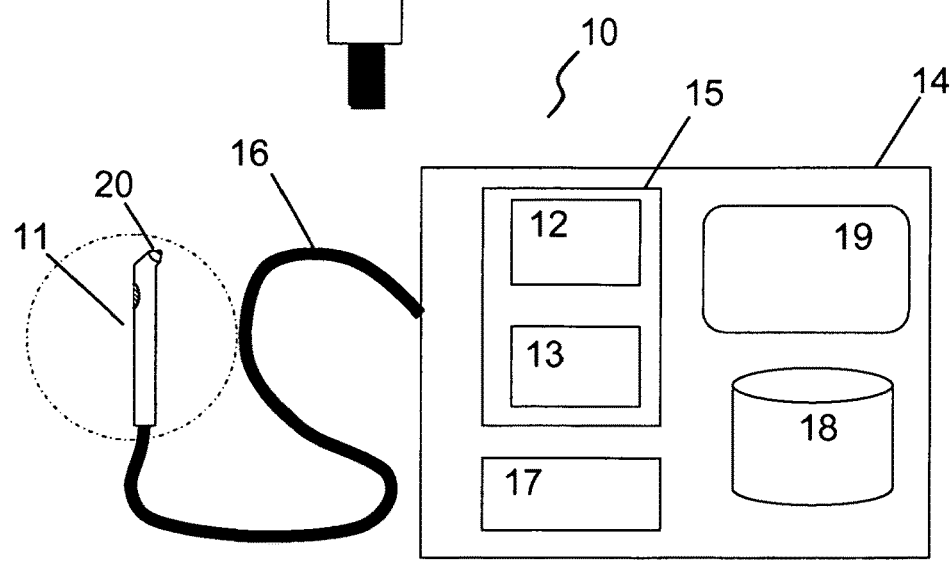

An embodiment of the invention is illustrated in FIG. 2A, showing a photonic probe apparatus 10 comprising a probe 11, a light source 12 connected to the probe for illuminating tissue, and a light sensor 13 connected to the probe to receive and detect light collected from the tissue region through the probe 11, preferably through a tip 20 of the probe. An analyzing unit 14 is connected to the light sensor 13 for determining whether a threshold measure of probability of a cancerous or precancerous lesion in the probed tissue region in contact with the probe is exceeded based on an output signal from the light sensor 13. The apparatus also comprises an integrated tissue marking facility (not shown in FIG. 2A) which can be activated to mark the probed tissue region through the probe when the threshold measure is exceeded.

The light source 12 may involve more light sources such as a combination of monochromatic and broad spectral light sources. The light source 12 may be integrated in the probe 11 in the form of small light sources such as light emitting diodes and diode lasers, or may be placed in a separate unit 15 of the apparatus, as shown in FIG. 2A, in the form of larger light sources such as lasers and lamps. Similarly, the light sensor 13 may involve a photodiode and potentially wavelength filters integrated in the probe 11, or may also be placed in the separate unit 15 as shown in FIG. 2A. In case of the light source and/or light sensor being placed in the unit 15 separate from the probe 11, they should be connected to the probe 11 by an optical guide 16 for illuminating tissue and collect light from tissue. Such optical guide 16 may involve optical components such as lenses, mirrors, prisms, gratings, diffractive optical elements, etc.

In a preferred embodiment, the analyzing unit 14 comprises an electronic processor 17 connected to receive the output signal from the light sensor 13; and a memory or electronic storage 18 holding a computer program configured to, when executed by the electronic processor: determining one or more measures of probability of a cancerous or precancerous lesion in the tissue region based on the output signal from the light sensor; and determining whether one or more of the determined measures of probability exceeds a predetermined threshold. The analyzing unit 14 can be a computer or a workstation or similar, and can involve an audio and/or visual output connected to the electronic processor, such as a display or monitor 19.

The optical guide 16 for illuminating tissue and for collecting light from tissue can be provided by one or more optical fibers. Using only one fiber for both purposes is advantageous as it simplifies the construction of the probe and the connection between probe and light source/sensor. Further, in the embodiment described later where the probe head scans by rotation, it provides the advantage that the optical guide can be made coincident with the axis of rotation, thereby simplifying the transmission of light through a rotating head.

The probe body can be rigid or flexible. A tip 20 of the probe 11 can be tilted away from an axis A of the probe as shown in FIG. 2B. This is advantageous as it makes it easier to probe tissue behind protrusions and in-between soft tissue and since it becomes easier for the user to rest his/her hand during the procedure.

In a preferred embodiment, the tip 20 involves a replaceable tip 21 shown in FIG. 2C, where the light source 12, light sensor 13, and the tissue marking facility works through the replaceable tip 21. Such tip is preferably formed in materials approved for medical applications and comprises, such as a plastic, and involves one or more light transmitting parts 22, 23, 24, 25 providing input and output for light and an output 26 for the tissue marking facility. The replaceable tip 21 should involve means (not shown) for attaching it to the probe 11 in a removable manner, and so that the light transmitting parts 22, 23, 24, 25 aligns with a light output (not shown) from and a light input (not shown) to the probe.

The tip 20 and the replaceable tip 21 can have similar layouts, and the embodiment shown in FIG. 2C is applicable to both. Here, transparent part 22 would connect to a source fiber for white light, transparent part 23 would connect to a source fiber for both laser light (to excite fluorescence) and for white light, while transparent parts 24 and 25 would connect to detection fibers guiding collected light (could be backscattered and/or fluorescent light) to the light detector 13 for detecting both visible light and for IR light.

Figure 3:
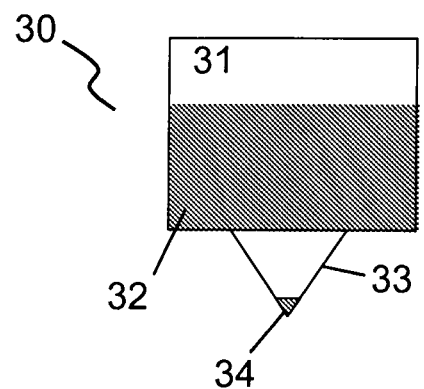
FIGS. 3 and 4 illustrate different embodiments of the tissue marking facilities.
Figure 4:
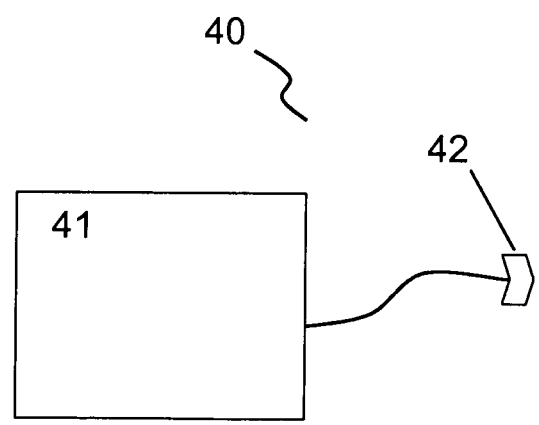

Different embodiments of the tissue marking facility are illustrated in FIGS. 3 and 4. In FIG. 3, the tissue marking facility 30 comprises a cartridge 31 for holding a marking substance 32 and means 33 for administering the marking substance through an output cannula 34 in the probe to dye tissue in contact with the probe. Different applicable and preferable marking substances have been described earlier.

The cartridge 31 can be integrated in the probe 11, or even in the replaceable tip 21 of the probe together with the output 34 (as output 26 in FIG. 2C). The location of the output cannula 34 or 26 in the center of the probe ensures the good marking resolution and avoids spilling of ink to other locations. Integrating the cartridge 31 in the replaceable tip 21 provides the advantages that there would be no need for refilling the cartridge, as it would be replaced together with the tip between each use. In such design, the cartridge would need to be small, which does not pose a problem since it would only need enough marking substance for a single use, typically a few mL. The means 33 for administering the marking substance can be electronically driven, and might be integrated in the probe rather than in the replaceable tip 21.

An alternative tissue marking facility 40 is illustrated in FIG. 4, and comprises an electric current source 41 connected to supply an output electrode 42 situated in the probe with sufficient current to coagulate tissue in contact with the probe as described previously. Again, the output of the tissue marking facility, here the electrode 42, can be integrated in the replaceable tip 21 as output 26, and connected to the current source 41 in, or via, the probe 11.

When probing and marking tissue, the probe may be held by hand or by a scanning mechanism. In a preferred embodiment, however, the probe involves an integrated scanning mechanism for moving at least part of the probe relative to the rest of the probe held by a user, and thereby relative to tissue of a patient. Such scanning mechanism provides the advantage of maintaining a proper speed of movement of the tip of the probe over the tissue, to allow time for both photonic detection and tissue marking without moving so slow that excessive marking is likely, such as by administering too much ink or seriously charcoaling tissue. This may be particularly relevant when probing and marking tissue that is to the user.

In a preferred embodiment of the scanning mechanism, a head 27 is rotatable mounted on the probe 11, and can be slowly rotated around axis A by the scanning mechanism (FIG. 2B). When marking tissue that is not directly visible, the head of the probe can be slowly inserted while rotating. This would for example be applicable in the endocervix, to mark the internal os. The probe body can have a button 28 for starting and stopping the scanning rotation of the head.

As described previously, the analyzing unit 14 determines a measure of probability of a cancerous or precancerous lesion in the probed tissue region based on the collected light. A number of applicable techniques for performing such analysis and determination is described in the prior art and will be summarized in the following. All of these use data analysis algorithms implemented by a software program stored in the memory of and executed by the processor of a computer.

A technique for estimation of lipid and water concentrations in scattering media with diffuse optical spectroscopy from 900 to 1600 nm is described by Nachabé et al. in Journal of Biomedical Optics, Vol 15, No 3p. 037015, 2010. Herein, both a photonic probe and a spectroscopy apparatus for gather and analyze data to obtain substance concentrations are described in detail. These techniques may be applied in the present invention for detecting substances that correlate well with a (pre)cancerous tissue state.

A technique for identifying a precancerous cervix in vivo based on diffuse optical spectroscopy is described by Chang et al., in Neoplasia Vol. 11, No. 4, p. 325, 2009. Here, a diffuse reflectance spectroscopy technique is applied to identify contrasts in optical biomarkers that vary with different grades of cervical intraepithelial neoplasia (CIN) from normal cervical tissues. The technique applies an optical probe and an instrument (with broadband light source, dispersive element, and detector), and a computer running a Monte Carlo algorithm to extract optical biomarker contributions including total hemoglobin (Hb) concentration, Hb saturation, and reduced scattering coefficient from the measured spectra. It is shown that concentration of oxyHb and total Hb increases significantly ($P<0.001$ and $P<0.002$, respectively) from normal and CIN 1 (grouped together) to CIN $2^+$. The instrumentation involves a fiber-optic probe, two spectrometers including Xenon lamps and monochromators. Light in the range 450 to 600 nm is collected and analyzed, but the used mathematical model is applicable over a wide wavelength range (from UV to visible). It is specifically mentioned that the physical illumination and collection geometry of the probe can be accurately accounted for in the model, thus allowing the technique to be implemented in the photonic probe apparatus according to the invention.

A technique for cervical precancer detection using a multivariate statistical algorithm based on laser-induced fluorescence spectra at multiple excitation wavelengths is described by Ramanujam et al. in Photochemistry and Photobiology, Vol. 64, No 4, p. 720, 1996. The technique applies a fluorimeter to acquire fluorescence spectra at 337, 380 and 460 nm excitation where after a multivariate statistical algorithm was used to extract clinically useful information from tissue spectra acquired in vivo. Two full-parameter algorithms were developed using tissue fluorescence emission spectra at all three excitation wavelengths for cervical precancer (squamous intraepithelial lesion (SIL)) detection. The algorithms involve a screening algorithm that discriminates between SIL and non-SIL and a diagnostic algorithm that differentiates high-grade SIL from non-high-grade SIL. The instrumentation involves a fiber-optic probe, two nitrogen-pumped dye laser producing illumination at 337, 380 and 460 nm, and a spectrograph.

A technique for near-infrared Raman spectroscopy for in vivo detection of cervical precancer is described in U.S. Pat. No. 5,991,653. The technique use algorithms based on empirically selected peak intensities, ratios of peak intensities and a combination of Principal Component Analysis (PCA) for data reduction and Fisher Discriminant Analysis (FDA). Normal tissues, inflammation and metaplasia were distinguishable from low grade and high grade precancers. The primary contributors to the tissue spectra appear to be collagen, nucleic acids, phospholipids and glucose 1-phosphate. The instrumentation involves an illumination device for generating at least one illumination wavelength of electromagnetic radiation selected to cause a tissue sample to emit a Raman spectrum comprising plurality of wavelengths shifted from the illumination wavelength. Typically, the light source is a laser. Also included is a Raman spectrum detector for detecting a plurality of peak intensities of the Raman spectrum at selected wavelength shifts. The system may further comprise a programmed computer connected to the Raman spectrum detector, programmed to compare each of the plurality of detected peak intensities with corresponding peak intensities of Raman spectra from normal tissue. It is also described how NIR Raman spectroscopy can be combined with fluorescence spectroscopy to improve the accuracy.

Although some of the above techniques are still in research, they show that an apparatus according to the invention with an analyzing unit distinguishing cancerous or precancerous tissue from normal tissue can be made. The references describes the techniques in much more detail than the summaries above, and each reference also describes how to implement an optical probe, light guides, light sources and sensors in relation to the analyzing unit.

Figure 5A:
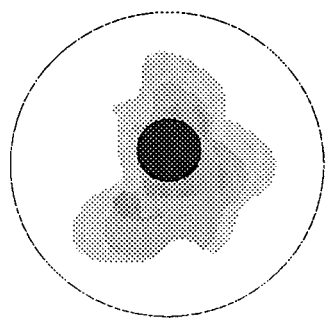
FIGS. 5A-F schematically depicts an excision procedure applying the marking method according to an embodiment of the invention and using a photonic probe apparatus according to an embodiment of the invention.
Figure 5B:
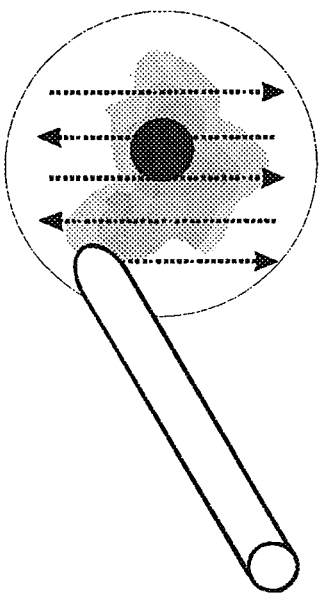
Figure 5C:
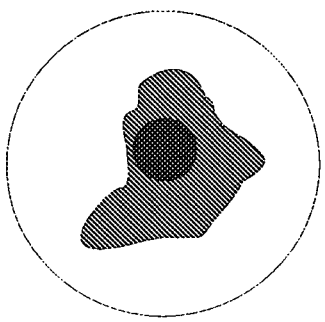
Figure 5D:
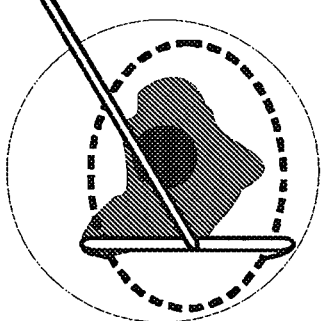
Figure 5E:
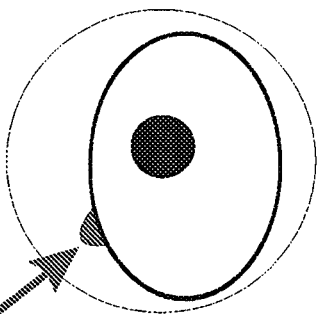
Figure 5F:
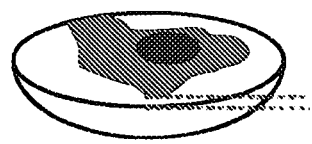
Figure 6:
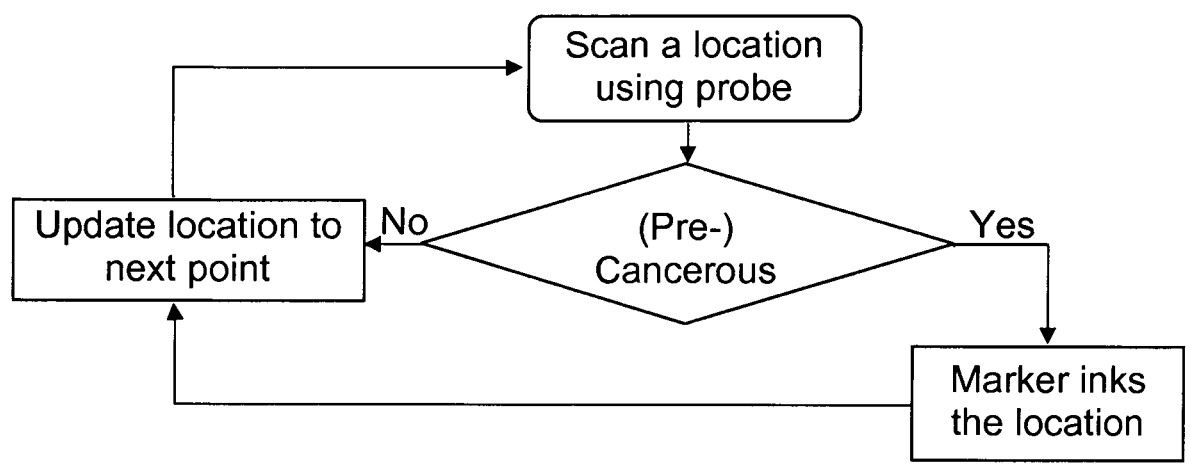
FIG. 6 is a flow diagram describing the procedure for marking up tissue in accordance with the use of the apparatus, and the method, according to the invention.

In the following, the use of the photonic probe apparatus and a method for marking a tissue region in a patient for excision will be described in more detail, referring first to FIGS. 2A and B, and later to FIGS. 5A-F and 6. The photonic probe apparatus will be used by the physician to scan the cervix of the patient prior to initiating an excision procedure. The probe will mark the extent (or alternatively just the borders) of the lesions either automatically or with input from the physician. The marking facility can thus work in two modes: manual or automatic. In manual mode the physician will be guided by the audio/video output such as screen 19, indicating whether the threshold measure is exceeded and can mark the present area by pressing a button 29 activating the tissue marker facility. In automatic mode the physician pre-specifies a threshold in the software program and the apparatus will automatically mark all areas exceeding that threshold. A brief overview of the workflow is shown in FIG. 6.

After the scanning phase the extent of the lesion is clearly visible to the physician, who can then proceed to excise the lesion. This will be described in relation to FIGS. 5A-F. The exact extent of the lesion is unclear (grey areas in FIG. 5A), so the physician scans with the probe over the whole cervix (FIG. 5B, only scanning of the ectocervix is depicted but in general the endocervix will be scanned as well). The probe clearly marks the extent of the lesion (FIG. 5C), so the physician can excise the tissue with confidence (FIG. 5D). If part of the marking is still visible on the patient's cervix (FIG. 5E) after excision, part of the lesion is still remaining and a re-excision is necessary. Such re-excision can be done without a new detection and marking since the marking is not transient. Also, by measuring the margins to the marked tissue on the excised tissue (FIG. 5F), one can check whether the excision margins are sufficient.

The apparatus and the method according to the invention are preferably adapted to, configured to or suitable for probing and possibly detection and marking of (pre)cancerous tissue regions in squamous and columnar epithelia. In particular, they are for doing this in the lower portion of the uterus, the cervix where the ectocervix is covered by a squamous epithelium consisting of multiple layers of cells, the endocervix is covered by a columnar epithelium consisting of a single layer of cells. The aspects of the invention are thereby preferably limited to detect and mark regions with cervical cancer or cervical intraepithelial neoplasia (CIN). The invention may also be applied for the resection of other types of cancer that originate in squamous epithelia (like e.g. oral cancer) or other pathological tissue as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advan-

The invention claimed is:

1. A photonic probe apparatus for marking biological tissue and comprising:
   a probe for transmitting light to tissue and collecting light from an illuminated tissue region in contact with the probe;
   a light source operably connected to the probe for illuminating tissue;
   a light sensor operably connected to the probe to receive and detect light collected from the tissue region in contact with the probe;
   an analyzing unit for determining a measure of probability of a cancerous or precancerous lesion in the tissue in contact with the probe and whether a threshold for the measure of probability of a cancerous or precancerous lesion in the tissue region in contact with the probe is exceeded based on an output signal from the light sensor; and
   an integrated tissue marking facility which can be activated to mark the tissue region in contact with the probe when the threshold measure is exceeded, wherein:
   the tissue marking facility comprises an electric current source connected to supply an output electrode situated in the probe with sufficient current to coagulate tissue in contact with the probe, and the probe comprises a replaceable probe tip wherein the light source, light sensor, and tissue marking facility works through the replaceable tip of the probe.

2. The photonic probe apparatus according to claim 1, wherein the analyzing unit comprises:
   an electronic processor connected to receive the output signal from the light sensor; and
   a memory holding a computer program configured to, when executed by the electronic processor:
   determine one or more measures of probability of a cancerous or precancerous lesion in the tissue region based on the output signal from the light sensor; and
   determine whether one or more of the determined measures of probability exceeds a predetermined threshold.

3. The photonic probe apparatus according to claim 1, wherein determining a measure of probability of cancerous or precancerous lesions involves distinguishing precancerous and/or cancerous tissue from not precancerous tissue based on the output signal from the light sensor.

4. The photonic probe apparatus according to claim 2, wherein the electronic processor is connected to control the tissue marking facility, and wherein the computer program is configured to automatically activate the tissue marking facility to mark tissue when the threshold measure is exceeded.

5. The photonic probe apparatus according to claim 2, further comprising an audio and/or visual output connected to the electronic processor, and wherein the computer program is configured to control the audio and/or visual output to indicate to a user whether the threshold measure is exceeded.

6. The photonic probe apparatus according to claim 1, wherein the probe further comprises an interface allowing a user to activate the integrated tissue marking facility to mark tissue.

7. The photonic probe apparatus according to claim 1, wherein the light sensor is configured to detect an intensity of collected light at different wavelengths to record a spectrum and wherein the threshold measure is related to the size of one or more peaks in the recorded spectrum.

8. The photonic probe apparatus according to claim 1, further comprising a scanning mechanism for moving at least part of the probe relative to tissue of a patient.

9. A replaceable tip of a probe for a photonic probe apparatus having an integrated tissue marking facility for marking biological/in vivo tissue, the tip comprises:
   one or more light transmitting parts;
   an output for a tissue marking facility for marking a tissue region in contact with the replaceable tip; and
   the one or more light transmitting parts aligning with a light output from and a light input to the probe, wherein:
   the output for the tissue marking facility comprises an electrode connected to an electric current source of the tissue marking facility, the output electrode being arranged to be in contact with the tissue region in contact with the replaceable tip when attached to the probe.

10. A method for marking a tissue region in a patient for excision, the method comprising:
    providing a probe for illuminating tissue and collecting light from an illuminated tissue region through the probe and a tissue marking facility having an output comprising an output electrode integrated in the probe;
    contacting tissue in the patient with the probe;
    emitting light from the probe to illuminate tissue;
    sensing and analyzing light collected from a tissue region in contact with the probe to determine a measure of probability of a cancerous or precancerous lesion in the tissue region in contact with the probe and whether a threshold measure of probability of a cancerous or precancerous lesion in the tissue region in contact with the probe is exceeded; and
    activating the tissue marking facility to mark the tissue region through the probe if the threshold measure is exceeded;
    wherein the tissue marking facility comprises an electric current source connected to supply the output electrode with sufficient current to coagulate tissue in contact with the probe;
    the probe comprises a replaceable probe tip wherein the light source, light sensor, and tissue marking facility works through the replaceable tip of the probe; and
    the marking step is a separate step from the sensing and analyzing steps and is performed after the sensing and analyzing steps.

* * * * *